US009441893B2

(12) United States Patent
Velayudhan et al.

(10) Patent No.: US 9,441,893 B2
(45) Date of Patent: Sep. 13, 2016

(54) THAWING VESSEL FOR BIOLOGICAL PRODUCTS

(71) Applicant: Grifols, S.A., Barcelona (ES)

(72) Inventors: Ajoy Velayudhan, Cary, NC (US); Robert Large, Raleigh, NC (US)

(73) Assignee: Grifols, S.A., Barcelona (ES)

( * ) Notice: Subject to any disclaimer, the term of this patent is extended or adjusted under 35 U.S.C. 154(b) by 841 days.

(21) Appl. No.: 13/803,128

(22) Filed: Mar. 14, 2013

(65) Prior Publication Data

US 2014/0026593 A1 Jan. 30, 2014

Related U.S. Application Data

(60) Provisional application No. 61/675,572, filed on Jul. 25, 2012.

(51) Int. Cl.

| | |
|---|---|
| ***F28F 13/12*** | (2006.01) |
| ***B01F 15/06*** | (2006.01) |
| ***C12N 1/04*** | (2006.01) |
| ***A01N 1/02*** | (2006.01) |

(52) U.S. Cl.

CPC ........... *F28F 13/125* (2013.01); *A01N 1/0242* (2013.01); *A01N 1/0284* (2013.01); *B01F 15/06* (2013.01); *B01F 15/063* (2013.01); *C12N 1/04* (2013.01)

(58) Field of Classification Search

CPC . F28F 13/125; A01N 1/0284; A01N 1/0242; C12N 1/04; B01F 15/06; B01F 15/063

See application file for complete search history.

(56) References Cited

U.S. PATENT DOCUMENTS 2,768,916 A * 10/1956 Seabold ................ C21D 9/561 148/287
3,427,011 A * 2/1969 Orcutt ....................... B01J 3/04 219/398
4,007,016 A * 2/1977 Weber ..................... B01F 7/169 366/144
4,028,527 A * 6/1977 Thagard, Jr. .............. C10C 3/12 126/343.5 A
4,158,742 A * 6/1979 Aldrich .................. F27B 17/02 219/410
4,336,435 A 6/1982 Kashyap et al.
4,670,397 A 6/1987 Hunt et al.
4,707,587 A * 11/1987 Greenblatt .............. A61M 5/44 165/102
5,205,128 A 4/1993 Richard
5,497,562 A * 3/1996 Pikus .................. C08G 63/785 34/266
5,914,255 A * 6/1999 Grae ...................... A23C 3/037 422/21
6,852,257 B2 * 2/2005 Eiva ........................ B29C 47/82 264/40.6
2004/0202587 A1 * 10/2004 Ashe .................... B01J 19/0013 422/109
2005/0011202 A1 1/2005 Voute et al.
2009/0166794 A1 7/2009 Mowry et al.
2010/0281886 A1 11/2010 Shaham et al.
2012/0073312 A1 3/2012 Cutting

FOREIGN PATENT DOCUMENTS

EP 0873781 8/2001
EP 1 665 930 A1 6/2006
WO WO 2005-023006 A2 3/2005

OTHER PUBLICATIONS

EPO, International Search Report in Application No. EP 13 17 6666, Feb. 7, 2014.

* cited by examiner

*Primary Examiner* — Tony G Soohoo
(74) *Attorney, Agent, or Firm* — RatnerPrestia

(57) ABSTRACT

Described herein are devices and methods for thawing frozen biological products efficiently without harming the products.

8 Claims, 3 Drawing Sheets

A
85
65
80
5
75
70
10
B
85
65
80
5
15
75
10
70
40
C
85
65
80
5
15
75
10
70
40
D
85
65
5
80
15
75
10
70
40

THAWING VESSEL FOR BIOLOGICAL PRODUCTS

The application is a complete application of U.S. Provisional Appln. Ser. No. 61/675,572, filed Jul. 25, 2012, incorporated herein by reference.

TECHNICAL FIELD

Described herein are devices and methods for thawing frozen biological products, e.g., potentially labile proteins and cells, efficiently without harming the products. In particular, a vertical thawing vessel with a plurality of independent thermal transfer means and temperature control means is described.

BACKGROUND

Biological products are often frozen after collection to preserve the components until further processing is carried out. Many collections are pooled and homogenized prior to freezing. When the frozen products are ready for additional processing, they must be carefully thawed to prevent overheating and deanaturation because some components are extremely sensitive to heat and can degrade during thawing. Thawing is often carried out in large vertical mixing vessels that have external jackets where heating media is circulated. Frozen products are added to the thawing vessel, are warmed, and thaw from thermal transfer through the walls of the jacketed vessel. The thawing product is typically stirred by a stirrer or impeller. Because the density of frozen, water-containing products is often less than the liquid form, the frozen maternal floats and collects at the top of the vessel, with the molten, thawed liquid transitioning to the lower portion of the vessel. One problem with such vertical thawing vessels is that the thawed liquid continues to be warmed after it has thawed and this can denature or degrade sensitive components. The apparatus and methods described herein overcome such shortcomings and provide a rapid and efficient means to thaw biological products without overheating and/or denaturing heat-sensitive components.

SUMMARY

Described herein are devices and methods for thawing frozen biological products, such as blood proteins and frozen cells, efficiently without harming the products.

One embodiment described herein is an apparatus for thawing frozen biological material, the apparatus comprising: a vessel having an interior space for receiving the biological material, the vessel having an upper portion extending around an upper portion of the interior space, and a lower portion extending around a lower portion of the interior space; a plurality of thermal transfer devices operatively associated with the vessel for transferring heat between the vessel and the thermal transfer device, comprising at least: a first thermal transfer device operatively associated with the upper portion of the vessel for transferring heat between the upper portion of the vessel and the first thermal transfer device; a second thermal transfer device operatively associated with the lower portion of the vessel for transferring heat between the lower portion of the vessel and the second thermal transfer device; and at least one controller operatively associated with the first and second thermal transfer devices for controlling the first and second thermal transfer devices independently from one another, comprising the at least one controller being adapted for controlling the first thermal transfer device to control thermal transfer between the first thermal transfer device and the upper portion of the vessel, and controlling the second thermal transfer device to control thermal transfer between the second thermal transfer device and the lower portion of the vessel.

In one aspect described herein, the number of thermal transfer devices is 2, 3, 4, 5, 6, 8, 10, 12, or even more.

In one aspect described herein, the apparatus for thawing frozen biological material further comprises at least one stirring apparatus and thermocouples extending into the interior space of the vessel, wherein: the thermocouples are arranged in an upwardly extending series; the thermocouples are operatively associated with the at least one controller; and the at least one controller is operative for controlling the first and second thermal transfer devices at least partially in response to signals from the thermocouples.

In one aspect described herein, the at least one controller comprises at least one processor and at least one memory including computer program code, and the at least one memory and the computer program code are configured to, with the processor, provide signals for: controlling the first and second thermal transfer devices independently from one another; controlling the first thermal transfer device to control thermal transfer between the first thermal transfer device and the upper portion of the vessel; and controlling the second thermal transfer device to control thermal transfer between the second thermal transfer device and the lower portion of the vessel.

In another aspect described herein, each of the first and second thermal transfer devices comprised a jacket mounted to an exterior of the vessel for providing at least conductive thermal transfer between the jacket and the vessel.

In another aspect described herein, the jacket extends around the vessel.

In another aspect described herein, the jacket comprises at least one passageway for having a thermal transfer fluid flow therethrough.

In another aspect described herein, the thermal transfer medium comprises a thermal transfer liquid.

In another aspect described herein, the apparatus comprises a system in fluid communication with at least one passageway for circulating the thermal transfer fluid through the passageway.

Another embodiment described herein is a method for thawing frozen biological material, comprising: introducing the frozen biological material into a vessel; causing thermal transfer between an upper portion of the vessel and medium exterior to the upper portion of the vessel, comprising heating the upper portion of the vessel; causing thermal transfer between a lower portion of the vessel and medium exterior to the lower portion of the vessel; monitoring temperature of the biological material at different levels in the vessel; adjusting the thermal transfer between the upper portion of the vessel and the medium exterior to the upper portion of the vessel at least partially in response to the monitoring of the temperature of the biological material; and adjusting the thermal transfer between the tower portion of the vessel and the medium exterior to the lower portion of the vessel at least partially in response to the monitoring of the temperature of the biological material, the adjusting of the thermal transfer between the lower portion of the vessel and the medium exterior to the lower portion of the vessel being performed independently of the adjusting of the thermal transfer between the upper portion of the vessel and the medium exterior to the upper portion of the vessel.

In one aspect described herein, the causing of the thermal transfer between the lower portion of the vessel and the medium exterior to the lower portion of the vessel comprises heating the lower portion of the vessel; and thereafter, the adjusting of the thermal transfer between the lower portion of the vessel and the medium exterior to the lower portion of the vessel comprises at least reducing the heating of the lower portion of the vessel.

In another aspect described herein, the causing of the thermal transfer between the lower portion of the vessel and the medium exterior to the lower portion of the vessel comprises heating the lower portion of the vessel; and thereafter, the adjusting of the thermal transfer between the lower portion of the vessel and the medium exterior to the lower portion of the vessel comprises cooling the lower portion of the vessel.

In another aspect described herein, the adjusting of the thermal transfer between the upper portion of the vessel and the medium exterior to the upper portion of the vessel comprises automatically adjusting the thermal transfer between the upper portion of the vessel and the medium exterior to the upper portion of the vessel; and the adjusting the thermal transfer between the lower portion of the vessel and the medium exterior to the lower portion of the vessel comprises automatically adjusting the thermal transfer between the lower portion of the vessel and the medium exterior to the lower portion of the vessel.

In another aspect described herein, at least the adjusting of the thermal transfer between the upper portion of the vessel and the medium exterior to the upper portion of the vessel is computer-implemented; and at least the adjusting of the thermal transfer between the lower portion of the vessel and the medium exterior to the lower portion of the vessel is computer-implemented.

Another embodiment described herein is an apparatus for thawing frozen biological material, the apparatus comprising: a vessel having an interior space for receiving the biological material, the vessel having an upper portion extending around an upper portion of the interior space, a middle portion extending around a middle portion of the interior space, and a lower portion extending around a lower portion of the interior space; a plurality of thermal transfer devices operatively associated with the vessel for transferring heat between the vessel and the thermal transfer device, comprising at least: a first thermal transfer device operatively associated with the upper portion of the vessel for transferring heat between the upper portion of the vessel and the first thermal transfer device; a second thermal transfer device operatively associated with the upper middle portion of the vessel for transferring heat between the upper middle portion of the vessel and the second thermal transfer device; a third thermal transfer device operatively associated with the lower middle portion of the vessel for transferring heat between the lower middle portion of the vessel and the third thermal transfer device; and a fourth thermal transfer device operatively associated with the lower portion of the vessel for transferring heat between the lower portion of the vessel and the fourth thermal transfer device; and at least one controller operatively associated with the first, second, third, and fourth thermal transfer devices for controlling the first, second, third, and fourth thermal transfer devices independently from one another, comprising the at least one controller being adapted for controlling the first thermal transfer device to control thermal transfer between the first thermal transfer device and the upper portion of the vessel; controlling the second thermal transfer device to control thermal transfer between the second thermal transfer device and the upper middle portion of the vessel; controlling the third thermal transfer device to control thermal transfer between the third thermal transfer device and the lower middle portion of the vessel; and controlling the fourth thermal transfer device to control thermal transfer between the fourth thermal transfer device and the lower portion of the vessel.

In one aspect described herein, the number of thermal transfer devices is 2, 4, 5, 6, 8, 10, 12, or even more.

In one aspect described herein, the apparatus for thawing frozen biological material further comprises at least one stirring apparatus and thermocouples extending into the interior space of the vessel, wherein: the thermocouples are arranged in an upwardly extending series; the thermocouples are operatively associated with the at least one controller; and the at least one controller is operative for controlling the first, second, third, and fourth thermal transfer devices at least partially in response to signals from the thermocouples.

In another aspect described herein, the at least one controller comprises at least one processor and at least one memory including computer program code, and the at least one memory and the computer program code are configured to, with the processor, provide signals for: controlling the first, second, third, and fourth thermal transfer devices independently from one another; and controlling the first thermal transfer device to control thermal transfer between the first thermal transfer device and the upper portion of the vessel; controlling the second thermal transfer device to control thermal transfer between the second thermal transfer device and the upper middle portion of the vessel; controlling the third thermal transfer device to control thermal transfer between the third thermal transfer device and the lower middle portion of the vessel; and controlling the fourth thermal transfer device to control thermal transfer between the fourth thermal transfer device and the lower portion of the vessel.

In another aspect described herein, each of the first, second, third, and fourth thermal transfer devices composes a jacket mounted to an exterior of the vessel for providing at least conductive thermal transfer between the jacket and the vessel.

In another aspect described herein, the jacket extends around the vessel.

In another aspect described herein, the jacket comprises at least one passageway for having a thermal transfer medium flow therethrough.

In another aspect described herein, the thermal transfer medium comprises a thermal transfer liquid.

In one aspect described herein, the apparatus for thawing frozen biological material further comprises a system in fluid communication with the at least one passageway for circulating the thermal transfer medium through the passageway.

Another embodiment described herein is a method for thawing frozen biological material, comprising: introducing the frozen biological material into a vessel; causing thermal transfer between an upper portion of the vessel and medium exterior to the upper portion of the vessel, comprising heating the upper portion of the vessel; causing thermal transfer between an upper middle portion of the vessel and medium exterior to the upper middle portion of the vessel; causing thermal transfer between a lower middle portion of the vessel and medium exterior to the lower middle portion of the vessel; causing thermal transfer between a lower portion of the vessel and medium exterior to the lower portion of the vessel; monitoring temperature of the biological material at different levels in the vessel; adjusting the thermal transfer between the upper portion of the vessel and the medium exterior to the upper portion of the vessel at least partially in response to the monitoring of the temperature of the biological material; the adjusting of the thermal transfer between the upper portion of the vessel and the medium exterior to the upper portion of the vessel being performed independently of the adjusting of the thermal transfer between the upper middle portion of the vessel and the medium exterior to the upper middle portion of the vessel; the adjusting of the thermal transfer between the upper portion of the vessel and the medium exterior to the upper portion of the vessel being performed independently of the adjusting of the thermal transfer between the lower middle portion of the vessel and the medium exterior to the lower middle portion of the vessel; and the adjusting of the thermal transfer between the upper portion of the vessel and the medium exterior to the upper portion of the vessel being performed independently of the adjusting of the thermal transfer between the lower portion of the vessel and the medium exterior to the lower portion of the vessel; and adjusting the thermal transfer between the upper middle portion of the vessel and the medium exterior to the upper middle portion of the vessel at least partially in response to the monitoring of the temperature of the biological material; the adjusting of the thermal transfer between the upper middle portion of the vessel and the medium exterior to the upper middle portion of the vessel being performed independently of the adjusting of the thermal transfer between the upper portion of the vessel and the medium exterior to the upper portion of the vessel; the adjusting of the thermal transfer between the upper middle portion of the vessel and the medium exterior to the upper middle portion of the vessel being performed independently of the adjusting of the thermal transfer between the lower middle portion of the vessel and the medium exterior to the lower middle portion of the vessel; and the adjusting of the thermal transfer between the upper middle portion of the vessel and the medium exterior to the upper middle portion of the vessel being performed independently of the adjusting of the thermal transfer between the lower portion of the vessel and the medium exterior to the lower portion of the vessel; and adjusting the thermal transfer between the lower middle portion of the vessel and the medium exterior to the lower middle portion of the vessel at least partially in response to the monitoring of the temperature of the biological material; the adjusting of the thermal transfer between the lower middle portion of the vessel and the medium exterior to the lower middle portion of the vessel being performed independently of the adjusting of the thermal transfer between the upper portion of the vessel and the medium exterior to the upper portion of the vessel; the adjusting of the thermal transfer between the lower middle portion of the vessel and the medium exterior to the lower middle portion of the vessel being performed independently of the adjusting of the thermal transfer between the upper middle portion of the vessel and the medium exterior to the upper middle portion of the vessel; and the adjusting of the thermal transfer between the lower middle portion of the vessel and the medium exterior to the lower middle portion of the vessel being performed independently of the adjusting of the thermal transfer between the lower portion of the vessel and the medium exterior to the lower portion of the vessel; and the adjusting of the thermal transfer between the lower portion of the adjusting the thermal transfer between the lower portion of the vessel and the medium exterior to the lower portion of the vessel at least partially in response to the monitoring of the temperature of the biological material; vessel and the medium exterior to the lower portion of the vessel being performed independently of the adjusting of the thermal transfer between the upper portion of the vessel and the medium exterior to the upper portion of the vessel; the adjusting of the thermal transfer between the lower portion of the vessel and the medium exterior to the lower portion of the vessel being performed independently of the adjusting of the thermal transfer between the upper middle portion of the vessel and the medium exterior to the upper middle portion of the vessel; and the adjusting of the thermal transfer between the lower portion of the vessel and the medium exterior to the lower portion of the vessel being performed independently of the adjusting of the thermal transfer between the lower middle portion of the vessel and the medium exterior to the lower middle portion of the vessel.

In one aspect described herein, the causing of the thermal transfer between the upper portion of the vessel and the medium exterior to the upper portion of the vessel comprises heating the upper portion of the vessel; and thereafter, the adjusting of the thermal transfer between the upper portion of the vessel and the medium exterior to the upper portion of the vessel comprises at least reducing the heating of the upper portion of the vessel.

In one aspect described herein, the causing of the thermal transfer between the upper middle portion of the vessel and the medium exterior to the upper middle portion of the vessel comprises heating the upper middle portion of the vessel; and thereafter, the adjusting of the thermal transfer between the middle portion of the vessel and the medium exterior to the upper middle portion of the vessel comprises cooling the upper middle portion of the vessel.

In one aspect described herein, the causing of the thermal transfer between the lower middle portion of the vessel and the medium exterior to the lower middle portion of the vessel comprises heating the lower middle portion of the vessel; and thereafter, the adjusting of the thermal transfer between the lower middle portion of the vessel and the medium exterior to the lower middle portion of the vessel comprises cooling the lower middle portion of the vessel.

In one aspect described herein, the causing of the thermal transfer between the lower portion of the vessel and the medium exterior to the lower portion of the vessel comprises heating the lower portion of the vessel; and thereafter, the adjusting of the thermal transfer between the lower portion of the vessel and the medium exterior to the lower portion of the vessel comprises cooling the lower portion of the vessel.

In one aspect described herein, the adjusting of the thermal transfer between the upper portion of the vessel and the medium exterior to the upper portion of the vessel comprises automatically adjusting the thermal transfer between the upper portion of the vessel and the medium exterior to the upper portion of the vessel; the adjusting the thermal transfer between the upper middle portion of the vessel and the medium exterior to the upper middle portion of the vessel comprises automatically adjusting the thermal transfer between the upper middle portion of the vessel and the medium exterior to the upper middle portion of the vessel; the adjusting the thermal transfer between the lower middle portion of the vessel and the medium exterior to the lower middle portion of the vessel comprises automatically adjusting the thermal transfer between the lower middle portion of the vessel and the medium exterior to the lower middle portion of the vessel; and the adjusting the thermal transfer between the lower portion of the vessel and the medium exterior to the lower portion of the vessel comprises automatically adjusting the thermal transfer between the lower portion of the vessel and the medium exterior to the lower portion of the vessel.

In one aspect described herein, at least the adjusting of the thermal transfer between the upper portion of the vessel and the medium exterior to the upper portion of the vessel is computer-implemented; at least the adjusting of the thermal transfer between the upper middle portion of the vessel and the medium exterior to the upper middle portion of the vessel is computer-implemented; at least the adjusting of the thermal transfer between the lower middle portion of the vessel and the medium exterior to the lower middle portion of the vessel is computer-implemented; and at least the adjusting of the thermal transfer between the lower portion of the vessel and the medium exterior to the lower portion of the vessel is computer-implemented.

Another embodiment described herein is an apparatus for thawing frozen biological products comprising: at least one vessel; one or more stirring means; a plurality of thermal transfer means surrounding the vessel; and at least one means for temperature control.

In one aspect described herein, the plurality of thermal transfer means are vertically positioned from the bottom to the top of the vessel.

In another aspect described herein, the temperatures of the plurality of thermal transfer means are independently controlled.

In another aspect described herein, the apparatus for thawing frozen biological material further comprises further comprising a plurality of thermocouples.

In one aspect described herein, the plurality of thermocouples are vertically positioned from the bottom to the top of the vessel.

In another aspect described herein, the internal temperature of the vessel is measured using the plurality of vertically arranged thermocouples.

In one aspect described herein, the temperature of thermal transfer means is modulated by thermoelectric, Peltier, or liquid media.

In one aspect described herein, the temperature of thermal transfer means is modulated by liquid media.

In one aspect described herein, the liquid media comprises ethylene glycol.

In one aspect described herein, there are at least four thermal transfer means and at least four thermocouples; and wherein the thermal transfer means and thermocouples are vertically positioned within the thawing vessel.

In one aspect described herein, the temperatures of the plurality of thermal transfer means are raised to not more than about 10° C. above the melting point for the biological product until melting is completed, and wherein the temperature is maintained at about 2° C. after melting is completed.

In one aspect described herein, the temperatures of the plurality of thermal transfer means are raised to not more than about 8° C. when a temperature of less than about 2° C. is measured; and wherein the temperatures of the plurality of thermal transfer means are lowered to about 4° C. when a temperature greater than about 10° C. is measured.

Another embodiment described herein is a process for thawing a frozen biological product comprising: (a) introducing the frozen biological products into a vessel comprising one or more stirring means, a plurality of thermal transfer means; a plurality of thermocouples; and a means for temperature control; (b) continuously measuring the temperature at a plurality of levels within the vessel using the plurality of thermocouples; (c) heating the thermal transfer means adjacent to the frozen biological products at the same time mixing the contents of the vessel; (d) cooling the thermal transfer means adjacent to the thawed biological products at the same time mixing the contents of the vessel; (e) heating and/or cooling the thermal transfer means to compensate for the addition of additional frozen biological product and the thawing of the biological product.

DETAILED DESCRIPTION

Described herein are apparatuses and methods for thawing frozen biological products that could be fed in as frozen blocks or in other configurations. Exemplary frozen biological products comprise blood, various blood products such as plasma or serum, or frozen cells or tissues. Biological products can also comprise cell culture supernatants, cell extracts, homogenates, partially purified macromolecules, purified macromolecules, or therapeutic products.

Figure 1:
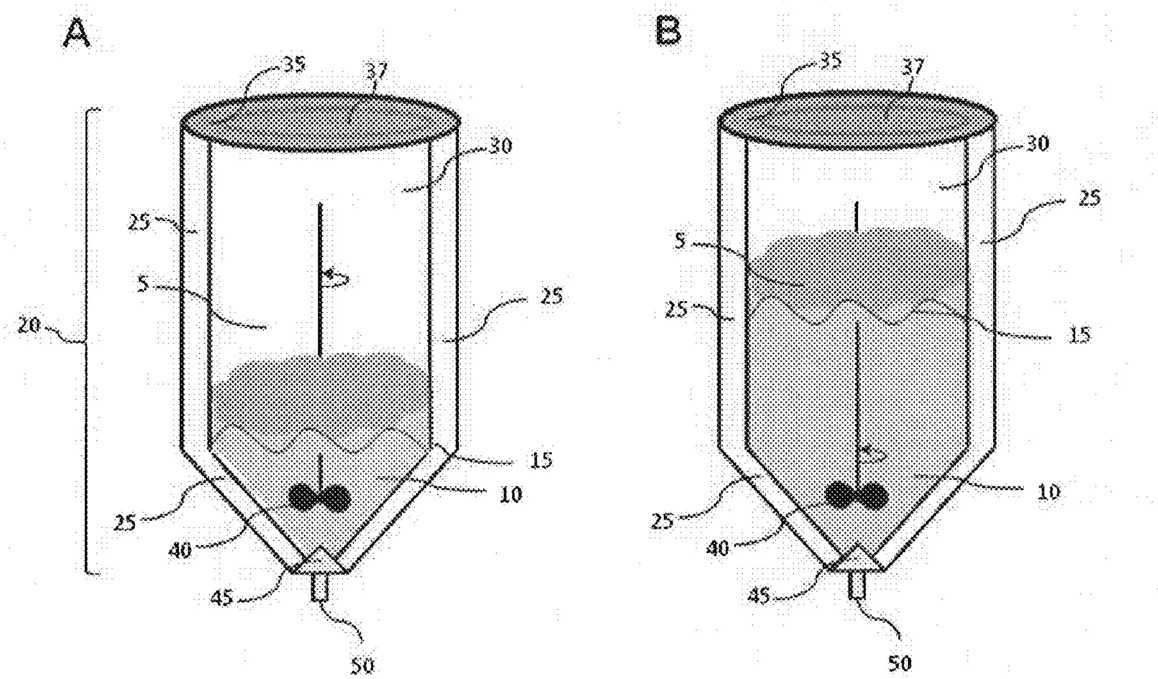
FIG. 1 illustrates a standard jacketed vertical thawing vessel shortly after addition of frozen biological product (A) and later after the majority of the biological product has thawed and liquefied (B).

A typical thawing vessel 20 is illustrated in FIG. 1. In this example, the frozen contents 5 in the interior of the closed vertical thawing vessel 30 are warmed by a jacketed exterior 25 that extends vertically around the vessel. A thermal medium, such as glycol or water is circulated through the jacket to increase the temperature. In FIG. 1A, the frozen biological product 5 is placed into the interior of the thawing vessel 30 through an opening 35, and the thermal medium is circulated to increase the temperature (thermal media and circulation means are known in the art and are not shown in the illustration). A top 37 covers the opening of the vessel. An impeller 40 circulates the thawed biological product liquid 10 and increases thermal transfer. A valve 45 and 50 spout can be used to remove the thawed biological product from the vessel after thawing is completed. As the frozen biological product 5 thaws and becomes liquid 10, the frozen biological product floats to the top of the level of liquid biological product 15 in the vessel. See FIG. 1B. The impeller 40 circulates the liquid product 10 and serves to transfer the warmed biological liquid up toward the remaining frozen product 5. In addition, the biological liquid is cooled near the frozen product and the impeller likewise circulates this cooled liquid. However, despite the circulation, a temperature gradient can establish within the thawed biological liquid because of the large surface area of the liquid in contact with the vessel interior. Further, as less frozen biological product exists, less of the frozen product is in contact with the vessel surface. Thus, the liquid biological product becomes the primary heat transfer medium to the frozen biological product. This can increase the time to complete thawing. Even if the temperature of the thermal medium is lowered or changed, the large thermal mass of thawed liquid makes rapid equilibration to the lowered temperature difficult. Consequently, the liquid biological can be unnecessarily exposed to increased temperatures for prolonged periods. This can cause denaturation and/or degradation of various components of the biological product. This is most pernicious for components such as proteins that may be sensitive to thermal denaturation. Accordingly, the thawing process can significantly reduce yields of valuable proteins that are thermally sensitive.

The multi-temperature thawing vessel as described herein overcomes the shortcomings of the existing thawing technology by permitting the user to fine-tune the temperature of the thawing vessel at various vertical levels and time points throughout the thawing process. Further, in some cases the multi-temperature thawing vessel as described herein may reduce the energy requirements for thawing biological products.

Figure 2:
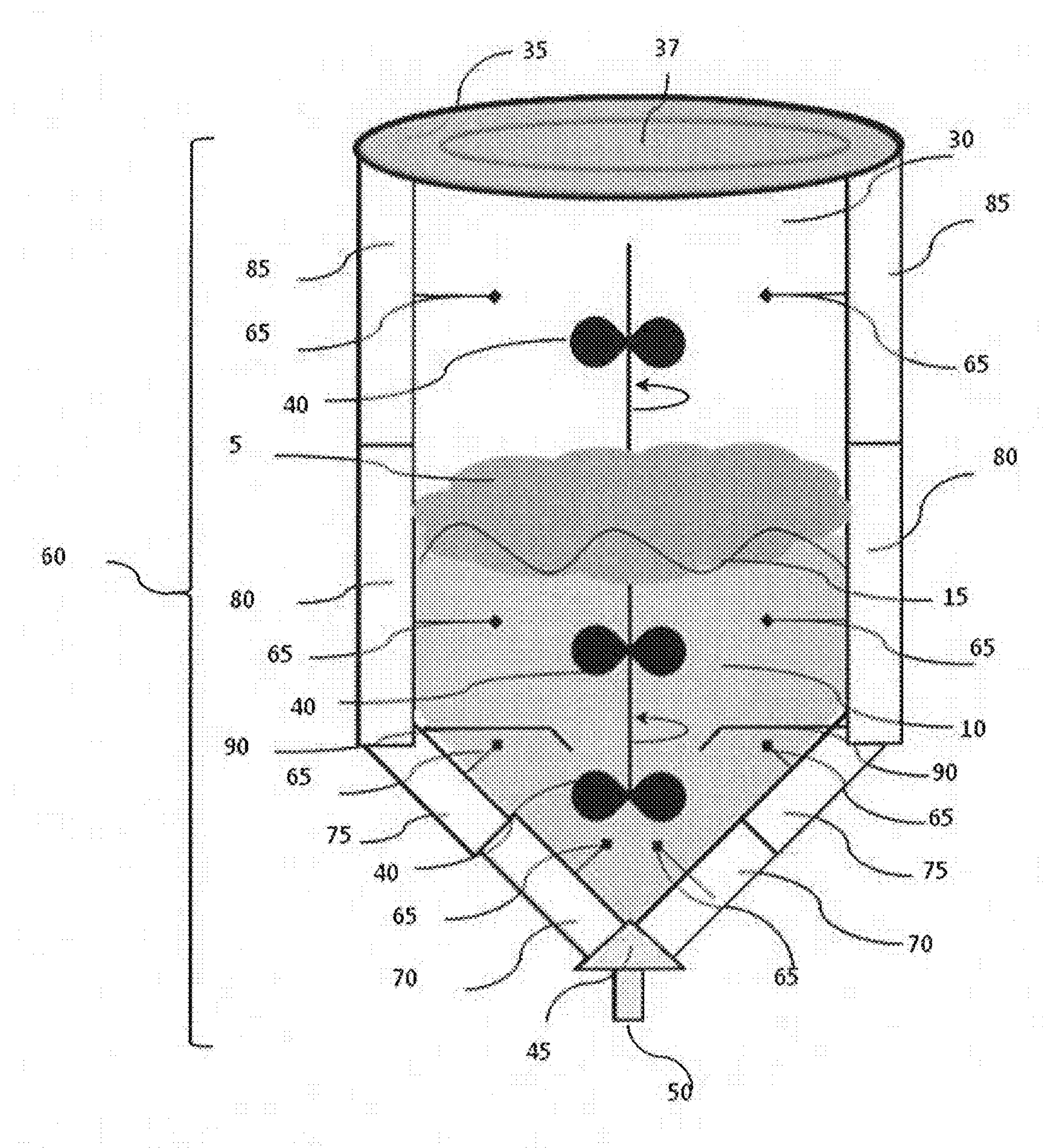
FIG. 2 illustrates a multi-jacketed vertical thawing vessel as described herein. This exemplary embodiment has four thermal transfer means vertically spaced from the bottom of the vessel to the top. Each thermal transfer means can heat or cool independently of the other thermal transfer means. In addition eight thermocouples extend into the vessel lumen near each thermal transfer means to measure the internal temperature. Baffles can be used to separate liquids stratified at each level.

An exemplary embodiment of the multi-temperature thawing vessel as described herein is illustrated in FIG. 2. This exemplary embodiment of a multi-temperature thawing vessel 60 features at least four independent thermal transfer means that are arranged vertically from the bottom of the vessel to the top of the vessel (70, 75, 80, 85). The number of thermal transfer means can vary. In some aspects, there may be 2, 3, 4, 5, 6, 8, 10, 12, or even more thermal transfer means associated with the vessel. Each thermal transfer means is capable of heating or cooling independent of the other thermal transfer means. In addition, at least two thermocouples 65 are positioned at each thermal transfer means level and extend outward toward the center of the vessel for measuring the temperature of the biological product medium at that level. Although the thawing vessel depicted in FIG. 2 is arranged vertically, a horizontal configuration is also contemplated. In a horizontal embodiment, a plurality thermal transfer means would be spaced from the bottom of the vessel to the top of the vessel, parallel to the axis of the cylinder. The thermal transfer means may be attached to the exterior walls of the vessel as shown in FIG. 2, or may be attached on the interior walls of the vessel. In some aspects, the thermal transfer means can comprise the walls of the vessel.

At least one impeller 40 circulates and mixes the liquefied biological product and thereby increases thermal transfer; the impeller also facilitates movement of the frozen biological product. Multiple impellers may be used. For example, at least one impeller can be used at each transfer means level. In some embodiments, baffles 90 can be used to reduce mixing of biological product at different thermal transfer means levels and thereby better control the temperature at each thermal transfer means level. In some embodiments, floating baffles can be used to separate the upper level of thawed biological product 15 liquid from the frozen biological product 5. As a non-limiting example, the baffles can comprise circular "doughnut-shaped" plates with hollow centers. Such a configuration would permit stratification of thawed biological product at each thermal transfer means level and permit limited transfer among levels.

A valve 45 and 50 spout permit removal of the thawed biological product from the vessel. The spout can be positioned at the bottom of the vessel as shown in FIG. 2 or may be at the top and removal is facilitated with a pump or siphoning means (not shown). Thawed biological product can be removed at the end of a thawing cycle or continuously during the thawing process to minimize exposure of the thawed biological product to elevated temperatures. The vessel can be configured so that as soon as the biological product is melted, it is removed from the thawing vessel.

In some embodiments, the thermal transfer means described herein can comprise jackets for circulating a thermal conducting liquid or gas. The liquid can comprise water, ethylene glycol, oil, or the like. Gases can comprise steam, $CO_2$, $N_2$, $O_2$, or refrigerant gas/liquid mixtures. The thermal transfer means can also comprise thermoelectric or Peltier devices. The thermal transfer devices typically are capable of supplying heating and/or cooling to the thawing vessel. In some case, the plurality of thermocouples can be used to monitor the internal temperature of the thawing vessel described herein and used to regulate the temperature of the thermal transfer means. In some aspects described herein, the temperature of the plurality of thermal transfer means are independently regulated by measuring the internal temperature of the thawing vessel using a plurality of thermocouples and then adjusting the internal temperature (i.e., raising or lowering the internal temperature) by adjusting the temperature of the thermal transfer means. In some aspects, this can be autonomously controlled by a computer. In other aspects, the temperatures are manually monitored and adjusted.

The multi-temperature thawing vessel as described herein permits the operator to precisely regulate the temperature of the thawing vessel walls at various levels and/or capacities. For example, as shown in FIG. 2, the thermal transfer means at the bottom of the vessel (i.e., 70 and 75) can be cooled, while the thermal transfer means 80 may be at an intermediate temperature and thermal transfer means 85 may be heated. This would facilitate thawing the frozen mass of biological product 5, which floats at the level of the thawed liquid 15. The thawed biological product liquid at the bottom of the vessel 10 is not subject to the heating thermal transfer means 85 or intermediate thermal transfer means 80 and thus the possibility of degradation or denaturation is reduced.

In addition, the multi-temperature thawing vessel as described herein can reduce the energy required to thaw biological products. Because the temperature is tightly controlled and monitored by thermocouples 65 at each thermal transfer means level, energy to heat/cool the thermal transfer means is only applied when necessary to heat/cool the region.

The multi-temperature thawing vessels as described herein has optimal thermal transfer efficiency when the frozen/thawed biological product is mixed as heating (or cooling) is applied. Thermal transfer is maximized as a function of the surface area to volume ratio. For a cylindrical vessel with height, h, and diameter, d, the surface area, SA, is: SA=πdh, and the volume, V, is $V=(\pi d^2h)/4$. Thus, the ratio of surface area to volume is: SA/V=4/d. Accordingly, as the diameter, d, is minimized, the ratio is maximized, and internal thermal transfer becomes highly efficient (with optimal mixing). As such, thawing vessels having small diameters can be particularly efficient with internal thermal transfer means. For example, a horizontal thawing vessel with stratified internal thermal transfer means can have very efficient thermal transfer.

EXAMPLES

Example 1

Figure 3:
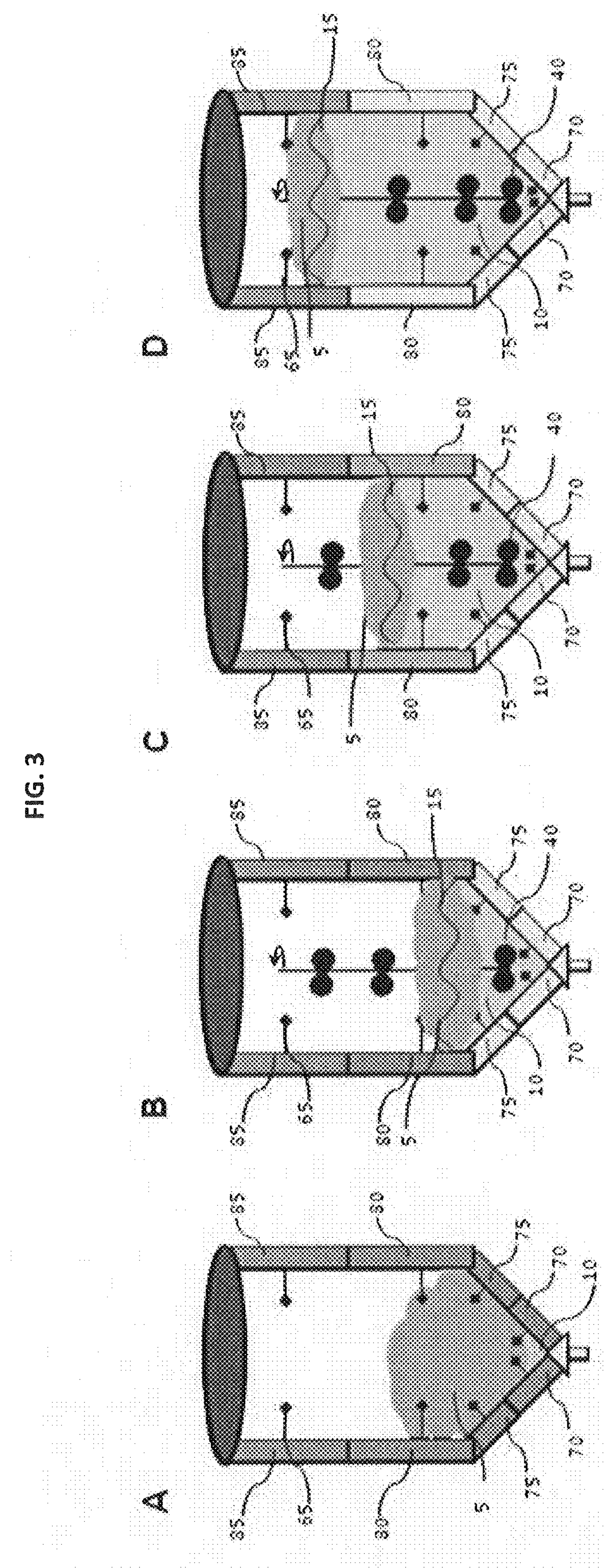
FIG. 3 illustrates an exemplary thawing process as described herein showing the independent heating or cooling of the respective thermal transfer means.

An exemplary process for thawing a biological product is illustrated in FIG. 3. At the beginning of the thawing process virtually all of the biological product is frozen. See FIG. 3A. Accordingly, all of the thermal transfer means (70, 75, 80,

85) can be adjusted to warm temperatures to facilitate melting of the frozen biological product 5. Note: in FIG. 3, the shading within the thermal transfer means (70, 75, 80, 85) indicates identical temperature at the shaded levels; darker shading indicates a relative higher temperature. The temperature within the thawing vessel can be monitored at various thermal transfer levels using the thermocouples 65. As the frozen biological product 5 begins to thaw, the liquid begins to collect at the bottom of the vessel. See FIG. 3B. Consequently, the temperature of the lower thermal transfer means (70, 75) can then be lowered and/or changed to cooling to prevent excess heating of the liquid biological product. The frozen biological product 5 floats atop the liquid biological product 15. Thus, the upper thermal transfer means (80, 85) can continue to warm the frozen biological product and facilitate thawing. As the frozen product thaws, the liquid level will rise and the temperature can accordingly be adjusted. Temperature measurements from the thermocouples at each level allow the operator to monitor the internal vessel temperature in real time. In some aspects described herein, the thawed biological product can be removed from the thawing vessel shortly after melting has occurred. An optimum rate of melting and removal of thawed produce can be established so that melting of the frozen biological product is maximized and removal from the thawing vessel is also optimized to prevent thermal denaturation of the biological product. The various modes of product removal, if at all, can be optimized for a specific biological product.

Later in the thawing process, the biological product exits in roughly equal proportions of frozen 5 and liquid 10 forms. See FIG. 3C. At this stage, three temperature levels can be utilized. The bottom thermal transfer means (70, 75) are cooled to prevent overheating of the biological product liquid. The middle thermal transfer means 80 can be set at an intermediate temperature (e.g., a median value between the warming temperature and the cooling temperature). This prevents the biological product liquid at the top of the liquid level 15 from being warmed too much. Baffles (not shown) can be used to further reduce thermal transfer from the upper level to the lower levels. The upper thermal transfer means 85 can continue to warm the frozen biological product.

At the final stages of the thawing process, most of the frozen biological product has been thawed to liquid and only a minor fraction exists in frozen form 5. See FIG. 3D. As such, the temperature of the upper thermal transfer means 85 can be lowered or remain warming. The middle thermal transfer means 80 can be lowered to cool or remain at an intermediate temperature level. When the frozen biological product is thawed, the thermal transfer means (70, 75, 80, 85) can be cooled to equilibrate the liquid biological product at an appropriate temperature for the next downstream process.

The scope of the devices and methods described herein includes all combinations of embodiments, aspects, examples, steps, and preferences herein described.

What is claimed is:

1. An apparatus for thawing a frozen biological material, the apparatus comprising:

a vessel having a biological material in an interior space of the vessel, the vessel having an upper portion extending around an upper portion of the interior space, a middle portion extending around a middle portion of the interior space and comprising an upper middle portion and a lower middle portion, and a lower portion extending around a lower portion of the interior space;

a plurality of thermal transfer devices operatively associated with the vessel for transferring heat between the vessel and the thermal transfer device, comprising at least:

a first thermal transfer device operatively associated with the upper portion of the vessel for transferring heat between the upper portion of the vessel and the first thermal transfer device;

a second thermal transfer device operatively associated with the upper middle portion of the vessel for transferring heat between the upper middle portion of the vessel and the second thermal transfer device;

a third thermal transfer device operatively associated with the lower middle portion of the vessel for transferring heat between the lower middle portion of the vessel and the third thermal transfer device; and a fourth thermal transfer device operatively associated with the lower portion of the vessel for transferring heat between the lower portion of the vessel and the fourth thermal transfer device; and at least one controller operatively associated with the first, second, third, and fourth thermal transfer devices for controlling the first, second, third, and fourth thermal transfer devices independently from one another, comprising the at least one controller being adapted for controlling the first thermal transfer device to control thermal transfer between the first thermal transfer device and the upper portion of the vessel;

controlling the second thermal transfer device to control thermal transfer between the second thermal transfer device and the upper middle portion of the vessel;

controlling the third thermal transfer device to control thermal transfer between the third thermal transfer device and the lower middle portion of the vessel; and controlling the fourth thermal transfer device to control thermal transfer between the fourth thermal transfer device and the lower portion of the vessel.

2. The apparatus of claim 1, further comprising at least one stirring apparatus and thermocouples extending into the interior space of the vessel, wherein:

the thermocouples are arranged in an upwardly extending series;

the thermocouples are operatively associated with the at least one controller; and the at least one controller is operative for controlling the first, second, third, and fourth thermal transfer devices at least partially in response to signals from the thermocouples.

3. The apparatus of claim 1, wherein the at least one controller comprises at least one processor and at least one memory including computer program code, and the at least one memory and the computer program code are configured to, with the processor, provide signals for:

controlling the first, second, third, and fourth thermal transfer devices independently from one another; and controlling the first thermal transfer device to control thermal transfer between the first thermal transfer device and the upper portion of the vessel;

controlling the second thermal transfer device to control thermal transfer between the second thermal transfer device and the upper middle portion of the vessel;

controlling the third thermal transfer device to control thermal transfer between the third thermal transfer device and the lower middle portion of the vessel; and controlling the fourth thermal transfer device to control thermal transfer between the fourth thermal transfer device and the lower portion of the vessel.

4. The apparatus of claim 1, wherein each of the first, second, third, and fourth thermal transfer devices comprises a jacket mounted to an exterior of the vessel for providing at least conductive thermal transfer between the jacket and the vessel.

5. The apparatus of claim 4, wherein the jacket extends around the vessel.

6. The apparatus of claim 4, wherein the jacket comprises at least one passageway for having a thermal transfer medium flow therethrough.

7. The apparatus of claim 6, wherein the thermal transfer medium comprises a thermal transfer liquid.

8. The apparatus of claim 6, comprising a system in fluid communication with the at least one passageway for circulating the thermal transfer medium through the passageway.

* * * * *